US009486427B2

(12) United States Patent
Gessler et al.

(10) Patent No.: US 9,486,427 B2
(45) Date of Patent: *Nov. 8, 2016

(54) ADMINISTRATION OF AEROSOLISED ILOPROST

(71) Applicant: VECTURA GMBH, Wittshire (GB)

(72) Inventors: Tobias Gessler, Wettenberg (DE); Thomas Schmehl, Gießen (DE); Werner Seeger, Biebertal (DE); Robert Voswinckel, Wettenberg (DE)

(73) Assignee: Vectura GMBH, Gauting (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/438,989

(22) PCT Filed: Sep. 12, 2013

(86) PCT No.: PCT/EP2013/068870
§ 371 (c)(1),
(2) Date: Apr. 28, 2015

(87) PCT Pub. No.: WO2014/067699
PCT Pub. Date: May 8, 2014

(65) Prior Publication Data
US 2015/0290153 A1    Oct. 15, 2015

Related U.S. Application Data

(60) Provisional application No. 61/720,733, filed on Oct. 31, 2012.

(30) Foreign Application Priority Data

Oct. 31, 2012 (EP) .................................... 12190832

(51) Int. Cl.
| | | |
|---|---|---|
| *A61K 31/191* | (2006.01) | |
| *A61M 15/00* | (2006.01) | |
| *A61K 9/00* | (2006.01) | |
| *G06F 19/00* | (2011.01) | |
| *A61K 9/12* | (2006.01) | |
| *A61K 31/5578* | (2006.01) | |

(52) U.S. Cl.
CPC ............ *A61K 31/191* (2013.01); *A61K 9/008* (2013.01); *A61K 9/0073* (2013.01); *A61K 9/0078* (2013.01); *A61K 9/12* (2013.01); *A61K 31/5578* (2013.01); *A61M 15/009* (2013.01); *A61M 15/0065* (2013.01); *A61M 15/0085* (2013.01); *G06F 19/3462* (2013.01)

(58) Field of Classification Search
None
See application file for complete search history.

(56) References Cited

U.S. PATENT DOCUMENTS

2012/0040945 A1    2/2012 Muellinger et al.
2014/0155486 A1*   6/2014 Gessler ............. A61K 31/5578
                                          514/573

FOREIGN PATENT DOCUMENTS

WO    WO2007/134292 A2    11/2007
WO    WO2010/008424 A2    1/2010

OTHER PUBLICATIONS

Olschewski et al., Chest (2003), 124(4), pp. 1294-1304.*
Braun, S., et al., "Evaluation of pulmonary vascular resonse to inhaled iloprost in heart transplant candidates with pulmonary venous hypertension," International Journal of Cardiology, No. 115, pp. 67-72 (2007).
Gessler, T. et al., "Ultrasonic versus jet nebulization of iloprost in severe pulmonary hypertension," European Respiratory Journal, vol. 17, pp. 14-19 (2001).
Ghofrani, Hossein Afdeschir et al., "Combination Therapy with Oral Siidenafil and Inhaled Iloprost for Severe Pulmonary Hypertension," American College of Physicians, vol. 136, No. 7, pp. 515-522 (2002).
Ghofrani, H.A. et al., "Amplification of the pulmonary vasodilatory response to inhaled iloprost by subthreshold phosphodiesterase types 3 and 4 inhibition in severe pulmonary hypertension," EMBASE (2002).
Kleemann Eike at al., "Iloprost-Containing Liposomes for Aerosol Application in Pulmonary Arterial Hypertension: Formulation Aspects and Stability," Pharmaceutical Research, vol. 24, No. 2. pp. 277-287 (2006).
International Search Report of International Application No. PCT/EP2013/068780, Nov. 29, 2013.
FDA (http://www.drugs.com/pro/ventavis.html, accessed Dec. 9, 2015).
Fischer, A. et al., "Novel Devices for Individualized Controlled Inhalation Can Optimize Aerosol Therapy in Efficacy, Patient Care and Power of clinical Trials," Eur. J. Med. Res., 14:71-77, (2009).
Hardaker, L.E., et al., "In vitro characterization of the I-neb Adaptive Aerosol Delivery (AAD) system," J. Aerosol Med. Pulm. Drug Deliv., Suppl. 1:S11-20 (2010).
Oischewski, H., "Inhaled Iloprost for the Treatment of Pulmonary Hypertension," Eur. Resp. Rev. 18:29-34, (2009).
The NTUH Drug Bulletin, vol. 27, No. 07 (Jul. 15, 2006).
Van Dyke et al., Respiratory Care 52:2, (2007), p. 184-190.

* cited by examiner

*Primary Examiner* — Brian J Davis
(74) *Attorney, Agent, or Firm* — Finnegan, Henderson, Farabow, Garrett & Dunner, L.L.P.

(57) ABSTRACT

The present invention relates to novel methods, compositions and kits useful for the treatment of pulmonary diseases such as pulmonary arterial hypertension. In particular, aerosolisable compositions of iloprost are provided which are for use in inhalation therapy. The administration is by inhalation over a short period of time, which is patient-friendly, effective, and well tolerated. Inhalation may, for example, be achieved using an efficient nebulizer based on the vibrating mesh technology.

13 Claims, 2 Drawing Sheets

ADMINISTRATION OF AEROSOLISED ILOPROST

This application is a national stage filing under 35 U.S.C. §371 of International Application No. PCT/EP2013/068870, filed on Sep. 12, 2013, which claims priority to European Patent Application No. 12190832.1, filed on Oct. 31, 2012, and also claims priority to U.S. Provisional Patent Application No. 61/720,733 filed on Oct. 31, 2012. The contents of these applications are each incorporated herein by reference.

FIELD OF THE INVENTION

The present invention relates to methods, compositions, and kits for the treatment of patients by aerosol therapy.

BACKGROUND OF THE INVENTION

Iloprost is a synthetic prostacyclin analogue. It mimics at least some of the biological activity of prostacyclin (also referred to as $PGI_2$ or epoprostenol) which is known to decrease arterial resistance, inhibit fibroblast growth, reduce platelet aggregation, and believed to be involved in anti-inflammatory and antimitogenic processes. The chemical name of iloprost according to IUPAC is 5-{(E)-(1S,5S,6R,7R)-7-hydroxy-6[(E)-(3S,4RS)-3-hydroxy-4-methyl-1-octen-6-inyl]-bi-cyclo[3.3.0]octan-3-ylidene}pentanoic acid, but it is also known as (E)-(3aS,4R,5R,6aS)-hexahydro-5-hydroxy-4-[(E)-(3S,4RS)-3-hydroxy-4-methyl-1-octen-6-ynyl]-$\Delta^{2(1H),\Delta}$-pentalenevaleric acid. More precisely, iloprost refers to the mixture of the 4R and 4S diastereomers at a ratio of approximately 53:47. It is an oily substance and soluble in methanol, ethanol, ethyl acetate, acetone and aqueous buffer at pH 7, sparingly soluble in aqueous buffer pH 9 and very slightly soluble in distilled water and aqueous buffer at pH 3 and pH 5. The molecular formula is $C_{22}H_{32}O_4$, which corresponds to a molecular weight of 360.49.

Iloprost is used in the therapy of pulmonary arterial hypertension, scleroderma, Raynaud's phenomenon and certain types of ischaemia. It is available as an aqueous inhalation solution (Ventavis®, sold by Actelion Pharmaceuticals in the USA and by Bayer Pharma in Europe and some other countries) for the aerosol treatment of pulmonary arterial hypertension. An injectable formulation of iloprost (Ilomedin®), also sold by Bayer Pharma and Actelion, is also used for the treatment of PAH. Ilomedin® is available in the form of 1 mL ampoules with an iloprost concentration of 20 µg/mL. In certain countries, other vial sizes and concentrations appear to be marketed as well.

According to the prescribing information for the US (version issued December 2011), the inactive ingredients in Ventavis® are tromethamine, ethanol, sodium chloride, hydrochloric acid for pH adjustment, and water for injection. The formulation may also be described as comprising iloprost in the form of iloprost tromethamine, i. e. the tromethamine salt of iloprost.

Pulmonary hypertension (PH) is a severe and potentially life-threatening disease characterised by an increase in blood pressure in the pulmonary circulation, typically associated with dizziness, fainting, shortness of breath, and exercise intolerance. Currently, pulmonary hypertension (PH) is classified by the WHO into 5 groups with pulmonary arterial hypertension (PAH) as group I. Pulmonary arterial hypertension may be further differentiated into idiopathic (IPAH) and heritable pulmonary arterial hypertension (HPAH) and other forms, the latter being induced by intake of drugs and toxins or associated with other diseases such as connective tissue diseases, HIV infection, portal hypertension, congenital heart disease, shistosomiasis or chronic haemolytic anaemia.

Prostacyclin and prostacyclin analogues are often considered as the most effective treatment options in particular for severe pulmonary arterial hypertension. Prostacyclin itself, or epoprostenol (Flolan®), is available as an injectable formulation which requires infusion through a central venous catheter. It is highly unstable and has to be cooled even during administration. A synthetic prostacyclin analogue which is more stable is treprostinil (Remodulin®) which can be administered intravenously or subcutaneously; however, subcutaneous injection is typically rather painful. Iloprost, which has a longer elimination half-life, may be administered intravenously (Ilomedin®) or by inhalation (Ventavis®). More recently, an inhalable form of treprostinil (Tyvaso®) was introduced to the market.

Inhalable iloprost (Ventavis®) is marketed in two strengths (10 µg/mL and 20 µg/mL, respectively), and administered from 6 to 9 times per day using the HaloLite® AAD®, the Prodose® AAD® inhaler system, the Venta Neb® or the I-neb® AAD® inhaler system. The Prodose® and HaloLite® inhalers are jet nebulisers which not marketed any more. The Venta Neb® is an ultrasonic nebulizer whereas the I-neb® system, which is the currently recommended inhalation system, is based on the more advanced vibrating mesh nebuliser technology. The administration of a single dose of 2.5 µg of iloprost using the formulation with 10 µg/mL of iloprost and one of the jet nebulisers takes about 4 to 5 minutes, that of a 5.0 µg dose approximately 8 to 10 minutes. The duration of administration is slightly shorter when using the I-neb® system, requiring about 3.2 minutes for the lower dose (2.5 µg) and about 6.5 minutes for the higher dose (5.0 µg), respectively (see Ventavis® 10 Mikrogramm/ml Lösung für einen Vernebler, Fachinformation, Bayer Pharma, July 2011). A single dose of 5 µg may also be administered using the formulation with 20 µg/mL of iloprost (in countries where this formulation is available), which takes approximately 4 minutes to inhale when using the I-neb® AAD® inhaler system. In practice, however, patients often experience longer inhalation times (10 to 15 min) than reported from controlled clinical trials.

In the context of inhalation treatment using Ventavis®, a single dose of 2.5 µg or 5.0 µg is generally understood as the dose of iloprost which is delivered from the inhalation device at the mouthpiece (see Ventavis® 10 Mikrogramm/ml Lösung für einen Vernebler, Fachinformation, Bayer Pharma, July 2011).

Considering the required frequency of administration and the duration of each administration cycle, the use of inhalable iloprost does not appear to be very convenient or patient-friendly.

However, a shorter time of administration through an increased aerosol delivery rate has been considered unfeasible in the past. In fact, when the suitability of an ultrasonic nebuliser having a high output rate for the administration of inhalable iloprost was tested, which could have potentially decreased the administration time significantly, researchers consented that, due to the expectation of serious adverse events, the concentration of iloprost in the inhalation solution had to be decreased so that the treatment remained sufficiently tolerable.

The strong bias against shortening the inhalation time in the case of iloprost is, for example, expressed by Gessler et al., Ultrasonic versus jet nebulization of iloprost in severe pulmonary hypertension, Eur. Respir. J. 17:14-19 (2001).

The authors state that on the basis of a comparison of the physical aerosol characteristics of the conventional jet nebuliser and the more efficient ultrasonic nebuliser there would have been the potential that in the case of the ultrasonic nebuliser the inhalation time for delivery of a single dose of 2.8 μg at the mouthpiece could have been reduced from 12 minutes to 2 minutes. However, this was considered to be therapeutically unfeasible, and the rapid inhalation had to be prevented because preliminary right heart catheter investigations had shown that adverse systemic effects (drop in blood pressure, decrease in systemic vascular resistance, flush, jaw pain, etc.) were associated with such rapid inhalation of iloprost. Therefore, the investigators decided to reduce the concentration of the iloprost inhalation solution from 10 μg/mL to 5 μg/mL when using the ultrasonic nebuliser, which resulted in an inhalation time of 4 minutes with this device.

Hence, therapy with inhalable iloprost remains inconvenient and time-consuming for patients. Thus there remains a need for improving the patient-friendliness of iloprost administration via the pulmonary route.

It is an object of the present invention to provide such improved therapy which is more convenient than the conventional treatment. In a further aspect, it is an object of the invention to provide methods, compositions, and kits for administering inhalable iloprost which overcome at least one of the disadvantages known from conventional iloprost aerosol therapy.

SUMMARY OF THE INVENTION

The invention provides a pharmaceutical composition of iloprost or a salt of iloprost which is used as an aerosol for pulmonary administration. It is characterised in that an effective single dose of the active ingredient is provided in aerosolised form for inhalation within 2 minutes or less. Moreover, the aerosol is administered in more than 12 breathing manoeuvres.

Inhalation therapy with iloprost according to the invention is different from a conventional nebulisation regimen in that a complete single dose is administered within a short period of time, such as within seconds or very few minutes. The aerosol is provided for inhalation by an inhalation device capable of delivering the aerosol at a sufficiently high output rate, such as a metered-dose inhaler, a soft mist inhaler, a powder inhaler, or a highly efficient nebuliser, e.g. a vibrating mesh nebuliser.

In a second aspect, the invention provides a pharmaceutical kit for use in inhalation therapy. The kit comprises a composition containing iloprost or a salt thereof and an inhaler that is adapted for providing an amount of the composition comprising an effective single dose of the active ingredient in aerosolised form for inhalation in more than 12 breathing manoeuvres and within 2 minutes or less. Also provided is a kit comprising an inhalable iloprost composition and an electronic data storage means capable of configuring an inhaler, or of controlling the operation of an inhaler, so as to provide an amount of the composition comprising an effective single dose of the active ingredient in aerosolised form for inhalation in more than 12 breathing manoeuvres and within 2 minutes or less.

In a further aspect, a method of treating a patient suffering from pulmonary arterial hypertension is provided. The method comprises the steps of (a) providing a pharmaceutical composition comprising iloprost or a salt thereof; (b) providing an inhaler adapted for delivering an amount of the composition comprising an effective single dose of the active ingredient in aerosolised form for inhalation in more than 12 breathing manoeuvres and within 2 minutes or less; and (c) administering the composition as an aerosol to the patient by using the inhaler.

Further aspects and embodiments will become clear on the basis of the detailed description below, the examples, and the patent claims.

DETAILED DESCRIPTION OF THE INVENTION

In a first aspect, the invention provides a pharmaceutical composition of iloprost or a salt of iloprost which is used as an aerosol for pulmonary administration. It is characterised in that an effective single dose of the active ingredient is provided in aerosolised form for inhalation within 2 minutes or less.

Iloprost is also known by its chemical name, which is 5-{(E)-(1S,5S,6R,7R)-7-hydroxy-6 [(E)-(3S,4RS)-3-hydroxy-4-methyl-1-octen-6-inyl]-bi-cyclo[3.3.0]octan-3-ylidene}pentanoic acid or (E)-(3aS,4R,5R,6aS)-hexahydro-5-hydroxy-4-[(E)-(3S,4RS)-3-hydroxy-4-methyl-1-octen-6-ynyl]-$\Delta^{2(1H),\Delta}$-pentalene valeric acid. In its currently used form, it consists of a mixture of the 4R and 4S diastereomers at a ratio of approximately 53:47. However, the invention may also be carried out with other diastereomer ratios, alternative isomers, and pharmaceutically acceptable salts of iloprost, such as the tromethamine salt.

The composition is used as an aerosol for pulmonary administration. As used herein, an aerosol is a dispersion of a solid or liquid phase in a gas phase. The dispersed phase, also termed the discontinuous phase, is comprised of multiple solid or liquid particles. In general, the particle size of the dispersed phase is typically (considerably) less than about 100 μm. Both basic physical types of aerosols, i.e. solid and liquid dispersions in a gas phase, may be used as pharmaceutical aerosols. Examples of aerosols representing solid particles in a gas phase are those emitted by dry powder inhalers (DPI's). In contrast, pressurised metered-dose inhalers, soft mist inhalers and nebulisers deliver aerosols whose dispersed phase is liquid. Pulmonary administration of an aerosol is achieved when a suitable inhalation device is used for generating an aerosol which is then inhaled by a subject by nasal or—more typically and also preferred according to the invention—by oral inhalation via a suitable mouthpiece.

A key feature of the invention is that the composition is inhaled within a short period of time, which is substantially different from a conventional nebulisation regimen, such as that used in the current inhalation therapy with iloprost. According to the invention, a complete single dose is administered within seconds or very few minutes. Such inhalation regimen is achieved by selecting a sufficiently high strength of the respective composition and by selecting an inhaler which is capable of, and actually adapted or configured for, emitting the composition in aerosolised form at such an output rate that the amount representing an effective single dose of the active ingredient is delivered within just seconds or very few minutes. In particular, the strength of the composition and the inhaler system are adapted to provide a single dose in aerosolised form which can be inhaled within 2 minutes or less. In further embodiments, the duration of administration is 2 minutes, 1½ minutes or less, 1 minute or less, and ½ a minute or less, respectively.

In the context of the present invention, ranges should be understood taking the normal variability of the respective parameters into account. For example, in the context of the duration of administration of a single dose of iloprost by inhalation, a period of 2 minutes is the same as a period commonly expressed as "about 2 minutes" or "approximately 2 minutes". Ranges for other parameters should be interpreted in a similar manner. For the avoidance of doubt, the terms "essentially", "about", "approximately" and the like in connection with an attribute or value should not be interpreted as excluding the exact or precise attribute or value.

Moreover, it is noted that according to the invention the aerosol is provided such as to enable the inhalation of a single dose within 2 minutes or less. This is based on the normal performance of breathing manoeuvres in inhalation therapy without interruptions. In other words, even if a patient should decide to interrupt the administration of a dose of iloprost, for example in the event of coughing or the like, leading to an extended time of administration, this would not exclude that a single dose is provided in aerosolised form for inhalation within a period of 2 minutes or less.

While the inhalation of a single dose of iloprost may be achieved with only a few breaths, or breathing manoeuvres, such as 12 deep breaths or less, it has been discovered by the inventors that patients who are unable of, or resistant to, performing breathing manoeuvres with large volumes of inhalation may also receive an effective dose of iloprost within 2 minutes or less. For example, the iloprost composition may be administered using an inhalation device which is configured to deliver a single dose with more than 12 relatively short breathing manoeuvres, such as with 13 to 25 breaths, or with 13 to 20 breaths, respectively. For example, a dose may be inhaled with 20 short breathing manoeuvres, each breathing manoeuvre having a duration of not more than 6 seconds, or with 24 short breathing manoeuvres having a duration of not more than 5 seconds each. In this context, the duration of a breathing manoeuvre should be understood as the typical, or average, duration of a breathing manoeuvre within a series of breathing manoeuvres.

Surprisingly, the inventors have found that pulmonary administration of iloprost according to the invention is technically and clinically feasible, and is actually well-tolerated by patients, in contrast to the negative bias and the expectations in prior art that such type of administration would be associated with severe adverse effects. The inventors have found that the desired haemodynamic effects (in terms of decrease in mean pulmonary arterial pressure and pulmonary vascular resistance) of administering 2.5 µg and 5 µg of iloprost, respectively, in the form of an aerosol inhaled according to the invention are comparable to those that were observed after the inhalation of the same doses over a time of 3.2 to 5 minutes (for 2.5 µg) or 6.5 to 10 minutes (for 5 µg) using the iloprost formulation having a concentration of 10 µg/mL; at the same time, the adverse effects, i.e. in terms of changes in systemic arterial pressure and systemic vascular resistance and good clinical tolerance, were also similar to those associated with the slow inhalation of iloprost.

Thus, the invention provides a novel use of inhalable iloprost which allows patients suffering from pulmonary arterial hypertension, regardless of e.g. whether they require single doses of 2.5 µg or 5 µg of iloprost, to benefit from short inhalation times which are much more convenient and better compatible with schedules and activities of a normal life compared to presently available therapeutic regimens.

Suitable inhalation devices for inhalation according to the invention include various types of modern inhalers based on different aerosolisation technologies. For example, a metered-dose inhaler (MDI or pMDI), a dry powder inhaler (DPI), a soft mist inhaler (SMI), or a modern, efficient nebuliser may be used. Metered-dose inhalers are typically pressurised, i.e. the active ingredient and optional inactive constituents are dispersed or dissolved in a liquid, pressurised propellant. An MDI typically comprises a canister which is usually of aluminium or stainless steel, a metering valve allowing a metered quantity of the formulation to be dispensed with each actuation, and an actuator which is often combined with a mouthpiece to allow the patient to operate the device and direct the aerosol into the patient's lungs via the mouth.

A powder inhaler, often referred to as dry powder inhaler (DPI), contains and dispenses a solid powder formulation which is emitted in aerosol form in metered quantities. Typically, DPIs rely on the force of patient inhalation to entrain powder from the device and subsequently break-up the powder into particles that are small enough to reach the lungs.

In a preferred embodiment, an efficient nebuliser is selected to carry out the present invention. Nebulisers may be subdivided into jet nebulisers, ultrasonic nebulisers, vibrating mesh nebulisers, and soft mist inhalers. Jet nebulisers use compressed air or gas to atomise or aerosolise a liquid drug formulation. They represent the most conventional type of nebuliser that is still used in inhalation therapy today. Jet nebulisers emit a rather diluted aerosol due to their high throughput of compressed air or gas which is needed for aerosol generation. It is believed by the inventors that most jet nebulisers would not be the most suitable devices to deliver an aerosol according to the invention as they have significant technical disadvantages, for example need of compressed air, dependency on power supply, high residual volume, etc.;

Ultrasonic nebulisers comprise an electronic oscillator which generates a high frequency ultrasonic wave causing mechanical vibration by which a liquid formulation is converted into a respirable aerosol. These nebulisers, which were introduced in the 1960s, were the first small, completely hand-held and almost silent nebulisers which improved the convenience of inhalation therapy. They are also typically capable of generating a denser, or more concentrated, aerosol which translates into a potentially higher output rate. Depending on the specific device and its configuration, it will be possible to carry out the present invention using an ultrasound nebuliser.

Vibrating mesh nebulisers, which were introduced only a few years ago, generate an aerosol from a liquid formulation by means of a vibrating mesh or membrane typically comprising several hundreds or even thousands of minute, mostly laser-drilled openings. While the liquid is squeezed through the openings, micron-sized aerosol droplets are generated. Vibrating mesh nebulisers are also small, hand-held devices. Typically, they emit very dense aerosols and therefore require much shorter inhalation times than e.g. conventional jet nebulisers, provided that formulations of comparable strengths are used. Vibrating mesh nebulisers represent one of the preferred types of inhaler by which the present invention is to be carried out. Examples of suitable and commercially available vibrating mesh nebulisers include Pari's eFlow, Respironics' i-Neb® AAD®, Omron's MicroAir®, Beurer's Nebulizer IH50®, Aerogen's Aeroneb®, and Activaero's AKITA² APIXNEB™.

With respect to the mesh used in such vibrating mesh nebuliser, it is preferred to select one which exhibits from about 900 to about 9,000 openings (or holes, or bores). More preferably, the mesh has at least about 2,000 openings, or at least about 3,000 openings, or at least about 4,000 openings, respectively. The diameter of the openings may, for example, be in the range from about 1.7 µm to about 2.8 µm.

Soft mist inhalers are sometimes considered as a subclass of nebulisers, as they convert non-pressurised liquid drug formulations into respirable aerosols, just like other nebulisers. On the other hand, they are also similar to metered-dose inhalers in that they generate their aerosol in metered quantities after actuation by the patient. An example of such a device is Boehringer's Respimat®, which uses the mechanical energy of the patient rotating the bottom of the device by 180° before each use. The rotation builds up tension in a spring around the flexible container holding the liquid drug formulation. When the patient actuates the device, energy from the spring is released and imposes pressure on the flexible container, whereby a portion of liquid is squeezed through two nozzles and emitted in aerosol form. In principle, also soft mist inhalers are suitable for practising the invention.

As mentioned, the inhalation device is selected from inhalers capable of delivering the aerosol at a sufficiently high output rate to enable inhalation according to the invention. In a preferred embodiment, the inhaler is selected from the group of metered-dose inhalers, soft mist inhalers, dry powder inhalers, and efficient hand-held nebulisers. In another preferred embodiment, the inhaler is selected from metered-dose inhalers, soft mist inhalers, vibrating mesh nebulisers, and ultrasonic nebulisers. Particularly preferred are vibrating mesh nebulisers and soft mist inhalers.

The selected nebuliser not only has to be capable of emitting a sufficiently dense aerosol to enable quick inhalation of iloprost, but it may also have to be adapted and/or configured accordingly. In the case of a vibrating mesh nebuliser, for example, the membrane (e.g. the number and size of its openings) must be selected to achieve the desired aerosol output in terms of aerosol quantity and quality.

In order to ensure a high degree of respirability, inhaler type and configuration are preferably selected to result in an aerosol having a volume median diameter, as measured by laser diffraction, in the range from about 1.5 µm to about 6 µm, and in particular from about 2.5 µm to about 5.5 µm, or even from about 3 µm to about 5 µm. It should be noted, however, that useful aerosol droplet size ranges also depend on the inspirational flow rate. For example, relatively large aerosol droplets of 4 to 6 µm in volume median diameter may still be highly suitable for pulmonary delivery if they are inhaled relatively slowly, e.g. using an inspirational flow rate of 20 L/min or less.

The geometric standard deviation indicates the dispersity of the aerosol droplet sizes. It is preferably in the range from about 1.2 to 3, and in particular from about 1.3 to about 2. In further embodiments, the geometric standard deviation is about 2 or less, or about 1.8 or less, or about 1.6 or less.

The inhalation device is preferably adapted to emit, or deliver to the patient via a mouthpiece, the aerosol at a moderate flow rate. Such moderate inspirational flow rate is advantageous as it reduces the fraction of aerosol droplets which are deposited in the upper airways, thus increasing the fraction of aerosol which is actually delivered to the deep lungs. According to the invention, the flow rate is preferably in the range from about 2 L/min to about 25 L/min, or from about 10 L/min to about 25 L/min, or even from about 10 L/min to about 20 L/min, such as about 15 L/min. This is in contrast to conventional breathing patterns by which patients often inhale nebulised aerosols at inspirational flow rates of 30 L/min or more.

Preferably, the device emits the aerosol only during the inhalation phase. As mentioned above, each breath, or breathing manoeuvre, is commonly understood to comprise an inhalation (or inspiratory) phase and an exhalation (or expiratory) phase. It is noted that many conventional inhalation devices emit their aerosol upon actuation or activation regardless of whether the patient inhales or exhales, whereas some more advanced devices are breath-controlled or breath-actuated and/or emit aerosol only while the patient inhales.

In a further preferred embodiment, the inhaler is selected and/or adapted to emit, for every inhalation phase of the patient to whom the aerosol is administered, a predetermined volume of aerosol-free air immediately following a predetermined volume of the aerosol. The air is provided over a period of about 0.2 to about 2 seconds at the end of each inhalation phase, typically corresponding to a volume of less than 100 mL to several hundred mL, depending on the inspirational flow rate. For example, a volume of about 250 mL of aerosol-free air may be emitted over a period of 1 second at a flow rate of 15 L/min.

In other words, instead of using the complete inhalation phase during a breathing manoeuvre to deliver aerosol from the inhaler, the inhalation phase may be divided into a first period in which aerosol is emitted and a second period in which no aerosol is emitted, but only air which is substantially aerosol-free. If the inhalation device is (or comprises) a nebuliser, the first period in which aerosol is emitted is also commonly referred to as nebulisation phase.

The effect of this technique of delivering air at the end of an inhalation phase is that the aerosol is targeted to the deeper parts of the respiratory system, whereas the aerosol-free air predominantly fills parts of the upper respiratory tract (oral cavity, larynx and pharynx) and the primary bronchi such as to reduce the deposition of the aerosol in these regions.

The duration of the first period of the inhalation phase of the breathing manoeuvre in which the aerosol is emitted from the inhalation device may be selected taking into account the condition of the patient, the possible inhalation volume, inspiratory capacity, forced expiratory volume inspirational flow rate and other factors. This period is optionally in the range from about 1 to about 4 seconds, or from about 1.5 to about 3 seconds, such as about 1.5, 2, 2.5, or 3 seconds, respectively. The total duration of the inhalation phase may, for example, be in range from about 2 to about 5 seconds, in particular from about 2.5 to about 4 seconds, such as 2.5, 3, 3.5 or 4 seconds. Useful is, for example, a nebulisation phase of 2 seconds followed by aerosol-free air being emitted for 1 second so that the total inhalation phase is 3 seconds.

The duration of the exhalation phase of the breathing manoeuver may depend on what the patients consider convenient. Often, it is rather similar (e.g. plus/minus 25%) to the inhalation phase if that is in the range of 2 to 5 seconds. For example. a complete breathing manoeuvre may last about 4 to 9 seconds, in particular from 5 to 8 seconds. An example of a useful breathing manoeuvre of a duration of 6 seconds is a combination of an inhalation phase of 3 seconds and an exhalation phase of 3 seconds, wherein the period of providing the nebulised aerosol during the inhalation phase is 2 seconds and the subsequent period of providing aerosol-free air is one second. However, other durations of the exhalation phase (and thereby of the breathing manoeuvre) are also feasible.

Such relatively short breathing manoeuvres may be particularly useful for certain patient groups, such as patients suffering from certain pulmonary diseases or conditions, or for any patients who may not be able to take deep breaths.

At an inspiratory flow rate of 15 L/min an inhalation phase of 3 seconds would correspond to an inhalation volume of 750 mL, which is feasible for most patients suffering from pulmonary arterial hypertension. If the nebulisation phase is 2 seconds, this means that about 500 mL of aerosol and 250 mL of aerosol-free air are inhaled. Of course, the amount of drug contained in this amount of aerosol will largely depend on the properties of the inhalation device and on the strength, or concentration, of the drug formulation. At an inspiratory flow rate of 30 L/min, an inhalation phase of 2.5 seconds would correspond to an inhalation volume of 1.250 mL. In case of this higher flow rate, a smaller droplet size with a VMD (volumetric median diameter) of e.g. 2.7 μm would be preferable. This smaller droplet size is somewhat more difficult to generate.

As mentioned, inhalation of iloprost according to the invention not only requires the selection and/or configuration of a suitable inhalation device, but also that of a suitable formulation of iloprost. In particular, the formulation should have a sufficiently high strength in order to enable administration of an effective single dose of iloprost (or a salt thereof) within a period of 2 minutes or less.

Depending on the specific patient, an effective single dose administered in one inhalation session may be in the range from about 1 μg to about 10 μg of iloprost, or from about 1.5 μg to about 5 μg of iloprost. Also preferred are single doses of about 2.5 μg and about 5 μg, as currently used in the therapy of pulmonary arterial hypertension. It is noted that these values are used to describe the amount of drug substance delivered to the mouthpiece of the inhaler. If an advanced nebuliser system with improved pulmonary deposition is used rather than a conventional nebuliser, it is also possible that lower doses than the currently used 2.5 μg and 5 μg, such as 1.5 to 2 μg instead of the conventional 2.5 μg dose, and 3 to 4 μg instead of the conventional 5 μg dose, are used. A single dose should preferably be accommodated in a volume of not more than about 1 mL. Optionally, it may be accommodated within a volume of not more than about 0.5 mL, such as in about 0.25 mL or less, or in about 0.1 mL or less. The currently marketed iloprost product for inhalation (Ventavis®) is available in two strengths, i.e. of 10 μg/mL and 20 μg/mL, respectively. In combination with an appropriate nebuliser, these strengths may be suitable for rapid administration of a single dose within 2 minutes or less. In some specific embodiments of the invention, an iloprost formulation having a strength of 10 μg/mL is used for delivering a single dose of 2.5 μg, and a formulation having a strength of 20 μg/mL is used for delivering a single dose of 2.5 μg or 5 μg, respectively.

At the same time, a higher strength in the range from higher than about 20 μg/mL to about 100 μg/mL could also be very useful for rapid inhalation. An aqueous iloprost formulation of 100 μg/mL is, for example, available in some countries as Ilomedin® (or Ilomedine®) concentrate for infusion.

As mentioned, iloprost administration according to the invention requires that an inhalation device is selected and/or configured to emit aerosol at a sufficient output rate (i.e. the rate by which the drug formulation is aerosolised and delivered at the mouthpiece of the device) in order to deliver an iloprost composition of a given strength within the specified time. For most aerosolisation technologies, the output rate is directly depended on particle size. One of the further advantages of certain embodiments of the invention is to allow inhalation of a larger droplets by using a low inspiratory flow rate.

In a specific embodiment, the iloprost composition is provided in liquid form and administered using an inhaler adapted to emit the composition in aerosolised form at an output rate of 0.4 mL/min or more, or at an output rate of 0.5 mL/min or more, such as 0.5 to 1.5 mL/min, or even more than 1.5 mL/min. These output rates are achievable, for example, by some modern nebulisers that use the vibrating-mesh technology. Such output rates are particularly useful when the invention is practised with the currently available iloprost formulations for inhalation having a strength of 10 and 20 μg/mL, respectively. An output rate of 1 mL/min in combination with a strength of 10 μg/mL would, for example, correspond to an iloprost delivery rate of 10 μg/min; consequently, a single dose of 2.5 μg of iloprost would require about 15 seconds of total nebulisation time, e.g. 4 breathing manoeuvres each having a nebulisation phase of slightly less than 4 seconds.

With respect to the iloprost delivery rate, it is one of the preferred embodiments that the inhaler is adapted to emit the composition in aerosolised form at a rate of at least about 2.5 μg of iloprost per minute, and optionally at a rate of at least about 5 μg of iloprost per minute. Optionally, the inhaler is adapted to deliver from about 5 to about 30 μg of iloprost per minute, using an iloprost formulation having a strength of about 10 or 20 μg/mL. For the avoidance of doubt, the expression "adapted to" means that the device is both capable of emitting, and configured to emit the aerosol in the specified manner. In another aspect, the invention is also directed to a nebulised aerosol itself. The aerosol comprises at least about 0.5 μg of iloprost or an equivalent amount of a salt thereof per liter of aerosol volume.

Preferably, the nebulised aerosol is emitted from a nebuliser at a rate from about 10 L/min to about 20 L/min. In other specific embodiments, the aerosol comprises about 1 μg to about 2 μg of iloprost in an aerosol volume of one liter, such as about 1.3 μg to 1.7 μg, and is emitted at an inspiratory flow rate of about 10 L/min to about 17 L/min. The aerosol is, in a particular embodiment, emitted at an output rate of 0.4 mL/min or more, such as about 0.5 to 1.5 mL/min, or even higher than 1.5 mL/min, at least during active nebulisation (i.e. not during any part of the inspiratory phase where no aerosol is emitted). In a further preferred embodiment, it is emitted at such a rate that an effective dose of about 2 μg to about 6 μg (in particular 2.5 μg or 5 μg)

delivered to the mouthpiece of the inhalation device is inhaled during no more than 4 breathing (or inhalation) manoeuvres, or even in not more than two breathing manoeuvres Moreover, the emitted aerosol is preferably followed by a predetermined volume of aerosol-free air, as described above. The volume of the aerosol may, for example, be selected to account for 20 to 50% of the total volume of inhalation during a breathing manoeuvre, or it may be 85% or less of the total volume of inhalation during one breathing manoeuver, the remaining volume being represented by aerosol-free air. Accordingly, the ratio of aerosol volume to the volume of aerosol-free air would be between 50:50 and 80:20, or it would be 85:15 or less, respectively. In another preferred embodiment, this ratio is about 75:25 or less.

The composition should be provided in sterile form and incorporate any necessary inactive ingredients to ensure an acceptable degree of stability, performance, and physiological tolerability. In one of the specific embodiments, the composition is in the form of an aqueous solution of iloprost, which is the preferred formulation design if a nebuliser or soft mist inhaler is used as inhalation device. Since the aqueous solubility of iloprost is rather poor, the incorporation of a solubilising excipient, such as an organic cosolvent, a pH-modifier, or a surfactant may be desirable. Examples of physiologically acceptable cosolvents suitable for inhalation, at least at a comparatively low concentration, are ethanol, glycerol, propylene glycol and polyethylene glycol. From these, ethanol is preferred. The composition should still comprise predominantly water as a solvent, e.g. amounting to at least 80 wt.-% of the liquid constituents.

Examples of potentially suitable surfactants include, in particular, phospholipids. Phospholipids can be defined as amphiphilic lipids which contain phosphorus. Also known as phosphatides, they play an important role in nature, in particular, as double layer-forming constituents of biological membranes. Phospholipids which are chemically derived from phosphatidic acid occur widely and are also commonly used for pharmaceutical purposes. Suitable phospholipids are also those which are suitable for administration by inhalation on account of their physiological properties. These comprise, in particular, phospholipid mixtures which are extracted in the form of lecithin from natural sources such as soy beans or egg yolk, preferably in hydrogenated form and/or purified, enriched or partially synthetically prepared phospholipids, preferably with saturated fatty acid esters.

Optionally, the composition may comprise further pharmaceutically acceptable excipients, such as isotonising agents, in particular inorganic salts; excipients for adjusting or buffering the pH, such as organic or inorganic salts, acids, and bases; sugars and sugar alcohols such as sucrose, lactose, mannitol, sorbitol, xylitol, and other sugar alcohols; stabilisers and antioxidants, such as vitamin E or vitamin E derivatives, or ascorbic acid; furthermore taste-masking agents, sweeteners, and flavours. In one of the preferred embodiments, one or more isotonising agents such as sodium chloride are incorporated in the composition to adjust the osmolality to a value in the range from about 200 mOsmol/kg to about 400 mOsmol/kg.

For adjusting and, optionally, buffering the pH, physiologically acceptable acids, bases, salts, and combinations of these may be used. Suitable excipients for lowering the pH value or as acidic components of a buffer system are mineral acids, in particular, sulphuric acid or hydrochloric acid. Moreover, inorganic and organic acids of medium strength as well as acidic salts may be used, for example, phosphoric acid, or citric acid. Suitable for raising the pH value or as basic component for buffer system are, in particular, mineral bases such as sodium hydroxide or other alkali and alkaline earth hydroxides and oxides, or tromethamine.

Optionally, the composition further comprises a stabilising agent, such as an antioxidant. Antioxidants are natural or synthetic substances which prevent or interrupt the oxidation of the active agents. These are primarily adjuvants which are oxidisable themselves or act as reducing agents, such as, for example, tocopherol acetate, lycopene, reduced glutathione, catalase, peroxide dismutase. Synergistic substances are, for example, those which do not directly act as reactance in oxidation processes, but which counteract in oxidation by an indirect mechanism such as the complexation of metal ions which act catalytically in the oxidation, which is the case, for example, for EDTA derivatives (EDTA: ethylenediamine tetraacetic acid). Further potentially suitable antioxidants include ascorbic acid, sodium ascorbate and other salts and esters of ascorbic acid (for example, ascorbyl palmitate).

The composition described herein is to be used for inhalation therapy, i.e. for pulmonary administration to a patient in need thereof. Patients who may benefit from the composition include those suffering from various forms of pulmonary hypertension (PH), such as pulmonary arterial hypertension (PAH). For example, it may be used for patients defined as the WHO Group I of patients suffering from pulmonary hypertension (Dana Point; California, US, 2008). This group comprises patients with PAH caused by various factors, including idiopathic (IPAH), heritable (HPAH), and associated with other diseases (APAH), such as connective tissue diseases, HIV infection, portal hypertension, congenital heart disease, shistosomiasis, chronic haemolytic anaemia, drugs and toxins, persistent pulmonary hypertension of the newborn, or other diseases or disorders. Moreover, it may be used for patients suffering from portopulmonary arterial hypertension, thromboembolic arterial hypertension, chronic thromboembolic arterial hypertension (CTEPH), and other forms of pulmonary hypertension.

According to a further option, the composition may be used for the treatment of patients with primary pulmonary hypertension or secondary pulmonary hypertension due to connective tissue disease or drug-induced, in moderate or severe stages of the disease; as well as moderate or severe secondary pulmonary hypertension due to chronic pulmonary thromboembolism, where surgery is not possible.

In particular, the product is to be used in patients exhibiting cardiovascular symptoms according to class II, III or IV (with some country-specific differences) of the functional classification of the New York Heart Association (NYHA). According to this scheme, class III symptoms are described as patients that are comfortable only at rest, with a marked limitation in activity due to symptoms, even during less-than-ordinary activity, e.g. walking short distances (20-100 m). Class IV relates to mostly bedbound patients with severe limitations who experience symptoms even while at rest.

It is also believed that the invention may be useful in the treatment of other forms of pulmonary hypertension (PH), such as—but not limited to—BMPR2, ALK1, endoglin (with or without hereditary hemorrhagic telangiectasia), PH or PAH with unknown origin, pulmonary veno-occlusive disease (PVOD) and/or pulmonary capillary hemangiomatosis (PCH); PH owing to left heart disease, e.g. systolic dysfunction, diastolic dysfunction, and/or valvular disease; PH owing to lung diseases and/or hypoxia, e.g. chronic obstructive pulmonary disease, interstitial lung disease, other pulmonary diseases with mixed restrictive and obstructive pattern, sleep-disordered breathing, alveolar hypoventilation disorders, chronic exposure to high altitude, and/or developmental abnormalities; PH with unclear multifactorial mechanisms, e.g. hematologic disorders such as myeloproliferative disorders, splenectomy; or systemic disorders such as sarcoidosis, pulmonary Langerhans cell histiocytosis, lymphangioleiomyomatosis, neurofibromatosis, vasculitis; or metabolic disorders such as glycogen storage disease, Gaucher disease, thyroid disorders; or other diseases such as tumoral obstruction, fibrosing mediastinitis, or chronic renal failure on dialysis.

The composition may be used as often as necessary in order to control the symptoms, but having regard to the limits of tolerability. Typically, several doses are administered per day, such as from 2 to 12 administrations (or dosings), and more preferably from 3 to 9 administrations, or from 6 to 9 administrations, respectively.

In a further aspect, the invention provides a kit which includes a composition as described above and an inhaler adapted for providing an amount of the composition comprising an effective single dose of the active ingredient in aerosolised form for inhalation within a period of 2 minutes or less. The composition is preferably provided in sterile containers each holding the amount required to administer a single dose of iloprost. Since the product will typically be used several times every day, a kit may comprise multiple single-dose containers comprising the composition. The inhaler, which may be any type of inhaler described above as useful for administering the composition, is adapted for emitting the composition in aerosolised form within 2 minutes or less, as explained above. Preferably, the inhaler in the kit is a highly efficient nebuliser, such as a vibrating mesh nebuliser.

Instead of the nebuliser, or in addition to it, the kit may also comprise an electronic data storage means which is capable of controlling the operation of an inhaler in such a way as to provide an amount of the composition comprising an effective single dose of the active ingredient in aerosolised form for inhalation according to the invention. In other words, some potentially suitable nebulisers may be adapted, configured, and/or controlled such as to deliver various types of aerosols, and it will be essential to adapt, configure, and/or control them in such a way that the administration regimen of the invention is enabled. This may be done manually or electronically. In one of the preferred embodiments, an electronic data storage means such as a programmable chip card is used for this purpose, and may therefore be included in the kit.

Moreover, the invention provides a method of treating a patient suffering from pulmonary arterial hypertension. The method comprises the steps of (a) providing a pharmaceutical composition comprising an active ingredient selected from iloprost and salts thereof; (b) providing an inhaler adapted for delivering an amount of the composition comprising an effective single dose of the active ingredient in aerosolised form for inhalation in more than 13 breaths and within a period of 2 minutes or less; and (c) administering the composition as an aerosol to the patient by using the inhaler. With respect the composition and the inhaler, reference is made to the features described above, which also apply in the context of the claimed method.

The invention is further illustrated by the following examples which should not be misunderstood as intending to limit the scope of the claimed subject-matter.

EXAMPLES

Example 1

In an in vitro nebulisation study, the feasibility of delivering aerosolised single doses of 2.5 µg and of 5 µg of iloprost to the mouthpiece of a nebuliser was evaluated. A nebuliser system comprising an electronic vibrating mesh nebuliser (by PARI GmbH, incorporating the Touchspray Technology®; having some similarity to PARI's eFlow® nebuliser) and a device for controlling the breathing pattern (AKITA®) was configured by means of an electronic chip card to deliver an aerosol from an aqueous solution at a flow rate of 15 L/min. The inhalation system is also known as AKITA$^2$ APIXNEB™ (by Activaero GmbH). For the purpose of enabling the control of the breathing pattern of a patient using the AKITA$^2$ unit, the nebuliser handset device in the APIXNEB™ system differs from the eFlow® system by modifications allowing it be connected to the AKITA$^2$ unit through an electric cord and an additional tube for providing e.g. a predetermined inspiratory air flow. Further details on the device may be taken e.g. from the Fact Sheet AKITA$^2$ APIXNEB™ (Art.-Nr. 05DK0105| V 1.0/Aufl.1). The inspiration time per breath was set at 4.1 seconds, corresponding to an inhalation volume of 1.025 mL. The nebulisation time was adjusted to 3.1 seconds, which corresponds to an aerosol volume of 775 mL. The device was also programmed to deliver 250 mL of aerosol-free air after emitting the aerosol during every inspiration cycle.

Two different meshes were used in the nebuliser. Both had around 3,000 openings of approx. 2 µm in diameter. Within the inhalation system used here, mesh A resulted in an aerosol with droplets having a volume median diameter (VMD) of 4.0 µm with a geometric standard deviation (GSD) of 1.47 when operated with isotonic sodium chloride solution, whereas mesh B exhibited a VMD of 4.1 µm and a GSD of 1.48.

Per test run an aliquot of 0.5 mL of an aqueous composition comprising 50 µg/mL of iloprost and the radiolabel $^{99m}$Tc in 0.9 wt.-% saline solution was filled into the fluid reservoir of the nebuliser. The inhaler system was activated to aerosolise the solution during series of four simulated breaths. The emitted aerosol was captured by inhalation filters, and the amount of aerosol was determined with a scintillation counter.

In result of two series of experiments, it was found that the mean amount of delivered aerosol for the first two breaths corresponded to 2.50 µg and 2.53 µg of iloprost, respectively, and the mean amount of delivered aerosol for all four breaths was 5.25 µg and 5.19 µg of iloprost, respectively. Thus the feasibility of delivering and inhaling a nebulised single dose of 2.5 µg of iloprost in only 2 breaths, and of 5 µg of iloprost in only four breaths, was clearly established.

Example 2

In an in vitro nebulisation study, the feasibility of delivering aerosolised single doses of 2.5 µg and of 5 µg of iloprost by inhalation according to the invention using three different inhalation devices and two different aqueous iloprost formulations was evaluated. The two tested formulations were the commercially available Ventavis® inhalation solutions 10 µg/mL and 20 µg/mL, respectively. At the same time, the resulting aerosol characteristics in terms of particle (droplet) size were determined.

The first inhalation device (A) was an AKITA$^2$ APIXNEB™ system as described in Example 1. The system was configured to provide an inspiratory flow rate of 15 L/min. The duration of each inhalation phase was 5 seconds, which period was divided into a nebulisation phase of 4 seconds immediately followed by a period of 1 second in which aerosol-free air was emitted. The duration of each exhalation phase was set as 5 seconds, so that the total duration of each breathing manoeuvre was 10 seconds.

The second inhalation device (B) was an eFlow® rapid (available from PARI GmbH), which is a vibrating-mesh nebuliser system that works in a continuous nebulisation mode, unlike the AKITA$^2$ APIXNEB™ system. In other words, the nebuliser continues to generate aerosol even during the exhalation phase. For the calculation of the expected inhalation times, it was assumed that a patient's breathing manoeuvre would consist of an inhalation phase and an exhalation phase of equal length. Since this device does not provide a controlled inspiratory flow at the mouthpiece, the setup for the test was according to DIN 13544 where a flow volume simulator (or breath simulator) is used to generate breathing manoeuvres with an inhalation volume of 500 mL, and where both the inhalation phase and the exhalation phase have a duration of 2 seconds. As this device does not control the breathing rhythm, the calculation of the numbers of breaths required to inhale a standard dose as well as the calculation of the total inhalation times were performed under the assumption that a patient would perform the breathing manoeuvres in 8 seconds each, with an inhalation phase and an exhalation phase of 4 seconds each.

The third inhalation device (C) was the prototype of a hand-held electronic inhaler comprising a vibrating-mesh nebuliser as described in co-pending European patent application no. 12 15 8852.9. In short, the device comprises a base part incorporating an electronic control unit and an air pump capable of ensuring an inspiratory flow rate in the desired range. A mixing channel, whose orientation is roughly horizontal, receives via a spherical upstream inlet opening a controlled air flow from the air pump. Before reaching the mixing channel, the air is filtered through a hydrophobic low flow resistance filter.

A vibrating-mesh aerosol generator protrudes approx. perpendicularly from a lateral (approx. superior) position into the mixing channel at the mixing zone, where the aerosol emitted from the aerosol generator and the air are mixed. Where the aerosol generator protrudes into the mixing channel, the channel abruptly narrows, in order to widen again continuously over about 8 cm towards the downstream end to form a tapered elliptical cylinder having an opening angle of approx. 5 to 6° which transitions into the mouthpiece. The reservoir holding the solution for nebulisation is located at the superior end of the aerosol generator.

The aerosol generator comprises a main member which is a turned part having a tubular portion whose outer area exhibits a ring-shaped widening. The main member extends through a ring-shaped piece of piezo-electric material. A perforated membrane is connected with the front end of the main member.

In analogy to device A, device C was configured such that each inhalation phase had a duration of 5 seconds, which period was divided into a nebulisation phase of 4 seconds immediately followed by a period of 1 second in which aerosol-free air was emitted. The duration of each exhalation phase was set as 5 seconds, so that the total duration of each breathing manoeuvre was 10 seconds.

For all inhalation devices, the aerosol output rates at the mouthpiece were determined by weighing in combination with both iloprost formulations. Assuming that the iloprost concentrations remained constant throughout the experiments (which is justified in view of the fact that the formulations were aqueous solutions with rather low solute concentrations), the delivery rates of iloprost at the mouthpiece were also calculated. The results are given in table 1.

TABLE 1

| | Device: | | | | | |
|---|---|---|---|---|---|---|
| | A | A | B | B | C | C |
| Iloprost conc. [µg/mL] | 10 | 20 | 10 | 20 | 10 | 20 |
| Ouput rate [mL/min] | 0.84 | 0.78 | 0.64 | 0.62 | 0.92 | 1.16 |
| Delivery rate [µg/s] | 0.14 | 0.26 | 0.11 | 0.21 | 0.15 | 0.39 |

From these results, the total nebulisation times required for delivering single doses of iloprost of 2.5 µg and 5 µg, respectively, were calculated. Assuming breathing manoeuvres with nebulisation phases of 4 seconds, the number of breaths required to deliver these doses were estimated. For each case, the total inhalation time was also calculated based on the assumption that the duration of each breathing manoeuvre is 10 seconds (devices A and C) or 8 seconds (device B). The respective figures are given in table 2 (iloprost dose: 2.5 µg) and table 3 (iloprost dose: 5.0 µg).

It should be noted that the total inhalation time may be calculated with respect to the final breathing manoeuvre in different ways which may lead to slightly different results. In tables 2 and 3, it was obtained by multiplying the calculated number of breaths with the duration of a breathing manoeuvre. Alternatively, the total inhalation time could be calculated taking into account the total length of the last breathing manoeuvre, as that last manoeuvre may be performed such as to consume the same time as any preceding breathing manoeuvre while only the nebulisation phase may be abbreviated to take into account that only a remaining fraction of the dose needs to be delivered. In other words, the total inhalation time would be calculated on the basis of the full number of breathing manoeuvres, rounded up to an integer. Optionally, the total inhalation time could also be calculated by taking only that fraction of the final breathing manoeuvre into account which is required to nebulise and inhale the last fraction of the drug dose. In this case, the calculated total inhalation time would be slightly shorter than given in tables 2 and 3.

TABLE 2

| | Device: | | | | | |
|---|---|---|---|---|---|---|
| | A | A | B | B | C | C |
| Iloprost conc. [µg/mL] | 10 | 20 | 10 | 20 | 10 | 20 |
| Nebulisation time [s] | 17.8 | 9.7 | 23.6 | 12.0 | 16.4 | 6.5 |
| No. of breaths required | 4.5 | 2.4 | 5.9 | 3.0 | 4.1 | 1.6 |
| Total inhalation time [s] | 44.5 | 24.2 | 47.2 | 24.0 | 41.0 | 16.1 |

TABLE 3

| | Device: | | | | | |
|---|---|---|---|---|---|---|
| | A | A | B | B | C | C |
| Iloprost conc. [µg/mL] | 10 | 20 | 10 | 20 | 10 | 20 |
| Nebulisation time [s] | 35.6 | 19.3 | 47.2 | 24.0 | 32.8 | 12.9 |
| No. of breaths required | 8.9 | 4.8 | 11.8 | 6.0 | 8.2 | 3.2 |
| Total inhalation time [s] | 89.1 | 48.3 | 94.4 | 48.0 | 81.9 | 32.3 |

Significantly, all inhalation devices allow inhalation of iloprost within a period of 2 minutes or less. Both iloprost solutions, i.e. with a strength of 10 μg/mL and 20 μg/mL, are suitable for this purpose. Particularly short and convenient treatment times result from using the 10 μg/mL strength for administering a 2.5 μg dose of iloprost, and from using the 20 μg/mL strength for administering a 2.5 or 5 μg dose.

For each device, the particle size distribution of the emitted aerosol using the iloprost composition having a strength of 10 μg/mL was also determined by laser diffraction, from which the expected pulmonary deposition pattern was calculated based on the ICRP deposition model (Human Respiratory Tract Model for Radiological Protection, ICRP Publication 66, Ann. ICRP 24, 1994; Guide for the Practical Application of the ICRP Human Respiratory Tract Model, ICRP Supporting Guidance 3, Ann. ICRP 32, 2002) using the software described by Koebrich et al. (1994). For the purpose of modelling, an age of 25 years and a functional residual capacity (FRV) of 3,300 mL were assumed.

The results of the deposition modelling are given in table 4. According to the model, the total deposition is the sum of the lung deposition and the extrathoracic deposition, which only excludes the fraction of the aerosol particles (droplets) which are emitted, inhaled and exhaled without deposition in any part of the respiratory system. Lung deposition may be differentiated into tracheobronchial, bronchial and alveolar deposition. In the context of the present invention, it is believed that a high fraction of alveolar deposition is particularly valuable in view of the desired therapeutic effect. As shown in table 4, all devices achieve a considerable degree of lung deposition, and devices A and C appear to be particularly useful in that they exhibit a very high degree of alveolar deposition.

TABLE 4

|  | Device: | | |
| --- | --- | --- | --- |
|  | A | B | C |
| Total deposition [%] | 89.4 | 60.3 | 92.1 |
| Extrathoracic deposition [%] | 10.1 | 14.6 | 10.3 |
| Tracheobronchial deposition [%] | 10.0 | 8.5 | 10.8 |
| Bronchial deposition [%] | 18.5 | 13.0 | 19.7 |
| Alveolar deposition [%] | 50.9 | 24.2 | 51.2 |

Example 3

A clinical pilot study to evaluate the safety and tolerability of nebulised iloprost administered by inhalation according to the invention was conducted with 4 patients. Eligible were male and female patients with pulmonary arterial hypertension in the age from 18 to 70 years having a mean pulmonary arterial blood pressure (PAP) higher than 25 mm Hg, a pulmonary vascular resistance (PVR) higher than 240 dyn*s*cm$^{-5}$, a central venous pressure (CVP) higher than 3 mm Hg, and a pulmonary capillary wedge pressure (PCWP) lower than 12 mm Hg.

Excluded were patients with a contraindication for cardiac catheterisation (such as coagulopathy, bleeding disorder, acute infection, severe cardiac dysrhythmia), pregnancy, systemic systolic blood pressure below 110 mm Hg, highly impaired ventricular function with cardiac index below 1.8 L/min*m$^2$, and known lack of pulmonary vascular reactivity.

Patients were monitored by ECG, pulse oxymetry, and non-invasive blood pressure measurement. An intracardiac catheter was introduced into the distal pulmonary artery to measure PAP, CVP, PCWP, and cardiac output. Also measured were the heart rate, systemic arterial pressure (SAP), systemic vascular resistance (SVR), central arterial and venous blood gases. After the initial determination of all parameters the reactivity of the pulmonary vasculature to oxygen (2 to 4 L/min) and nitric oxide (20 ppm) was tested.

Subsequently, patients inhaled a single dose of 2.5 μg of nebulised iloprost in two consecutive breaths, using the same inhalation system and iloprost composition as described in Example 1. Haemodynamics parameters and clinical condition of the patients were assessed before and up to 30 minutes after inhalation. In the absence of adverse effects, a second inhalation maneuver with 4 consecutive breaths corresponding to a dose 5 μg iloprost was performed, again followed by an observation period of at least 30 minutes.

Figure 1:
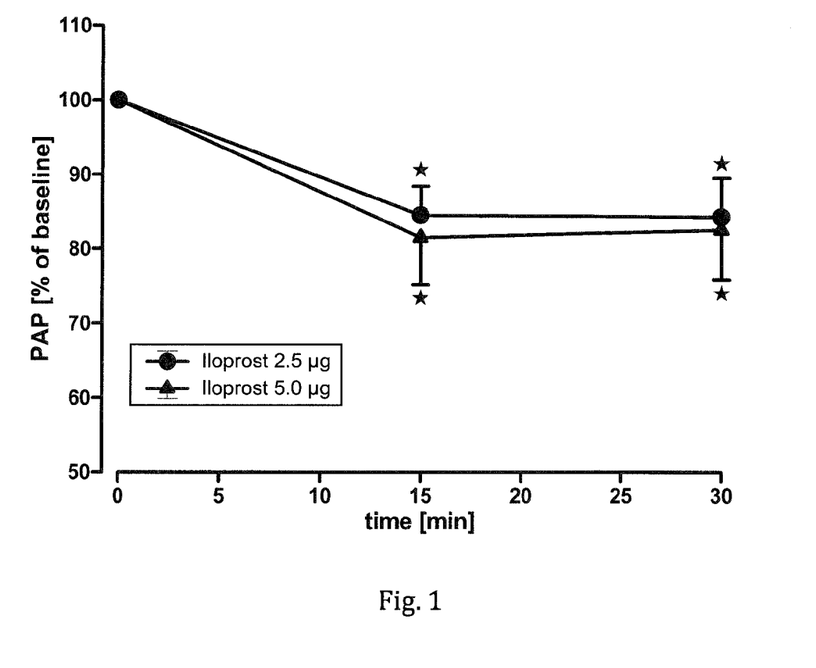
FIG. 1 shows the mean pulmonary arterial pressure (PAP) in patients with pulmonary arterial hypertension after inhalation of iloprost (0 min: baseline before inhalation); n=4; mean±SEM; * p<0.05, Mann-Whitney rank-sum test.
Figure 2:
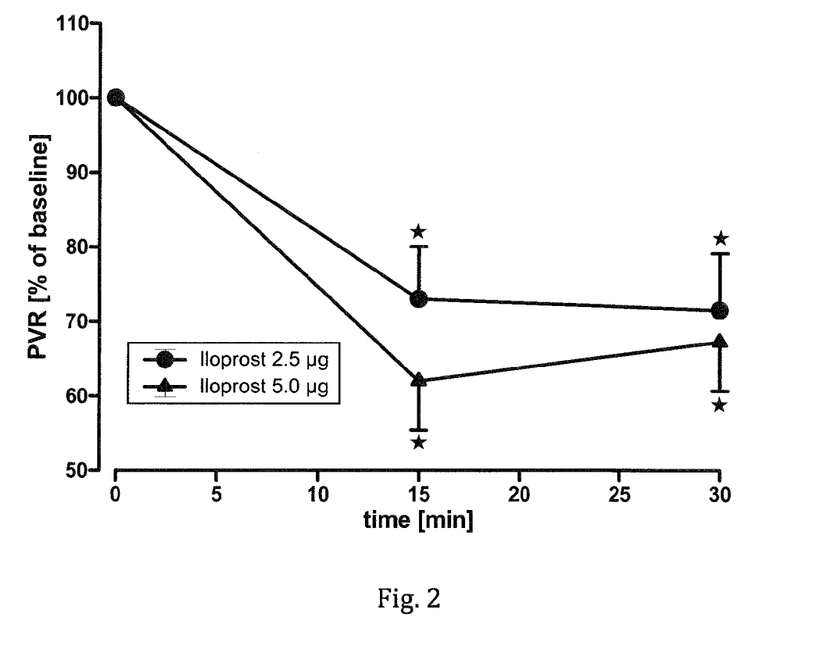
FIG. 2 shows the pulmonary vascular resistance (PVR) in patients with pulmonary arterial hypertension after inhalation of iloprost (0 min: baseline before inhalation); n=4, mean±SEM; * p<0.05, Mann-Whitney rank-sum test.
Figure 3:
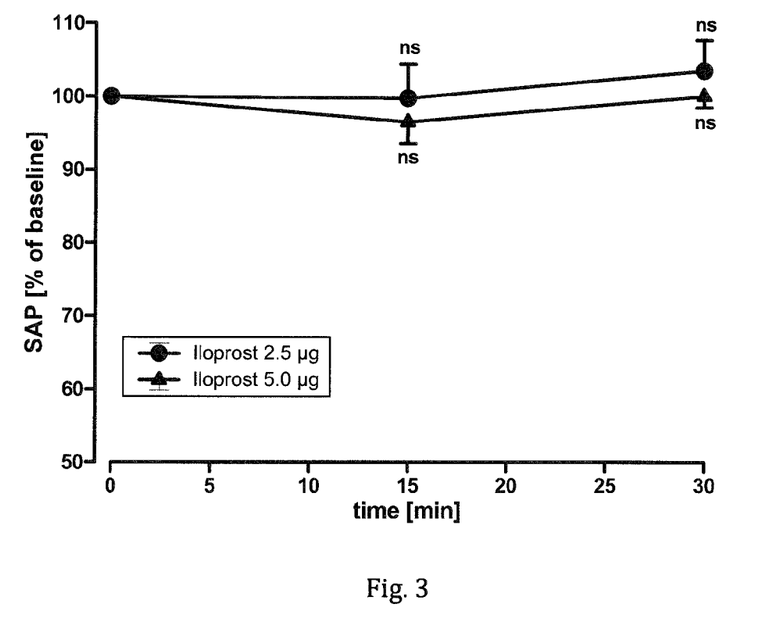
FIG. 3 shows the mean systemic arterial pressure (SAP) in patients with pulmonary arterial hypertension after inhalation of iloprost (0 min: baseline before inhalation); n=4, mean±SEM; ns: not significant, Mann-Whitney rank-sum test.
Figure 4:
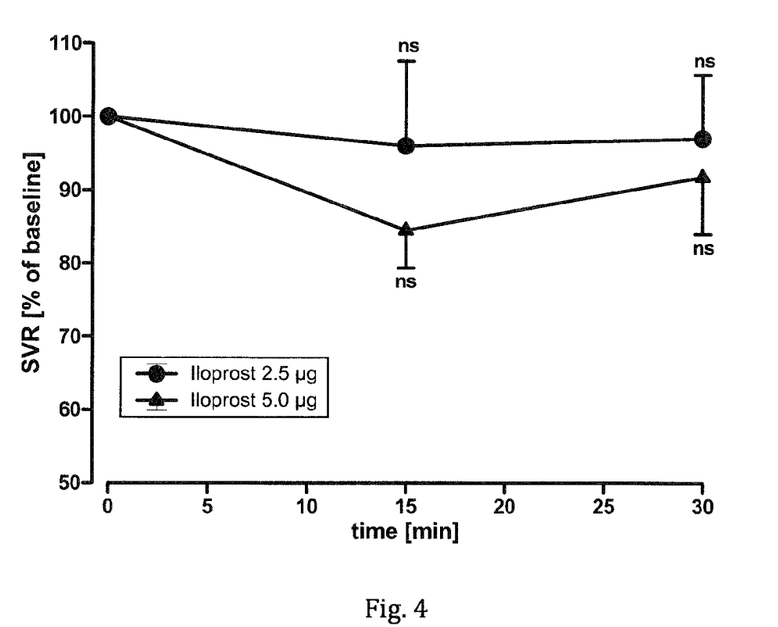
FIG. 4 shows the systemic vascular resistance (SVR) in patients with pulmonary arterial hypertension after inhalation of iloprost (0 min: baseline before inhalation); n=4; mean±SEM; ns: not significant, Mann-Whitney rank-sum test.

In result, it was found that all patients tolerated the treatment well. The therapeutic pulmonary vascular effects (as indicated by PAP and PVR changes, see FIG. 1 and FIG. 2) were comparable to those observed after conventional iloprost treatment, i.e. slow inhalation of iloprost. The same was true for the systemic side effects (as indicated by SAP and SVR changes, see FIG. 3 and FIG. 4).

For comparison, Olschewski et al. (Chest 2003; 124: 1294-1304) studied, inter alia, PAP, PVR, SAP, and SVR changes in response to conventional nebulisation and inhalation of 5 μg of iloprost over 10 to 12 minutes using three different nebulisers. They reported mean maximum PVR changes ranging from −38.0% to −36.4%, depending on the nebuliser that was used. Mean maximum PAP changes were −21.8% to −18.5%. The respective values for SAP changes ranged from −7.8% to −2.3%, and mean maximum SVR changes were from −24.6% to −17.0%, again depending on the specific nebuliser. Similar results were reported by Gessler et al. (Eur. Respir. J. 2001; 17:14-19).

Example 4

Six further patients suffering from pulmonary hypertension (PH) were treated with iloprost inhalation as in Example 3. These further patients exhibited various etiologies including pulmonary arterial hypertension (PAH), idiopathic pulmonary arterial hypertension (iPAH), portopulmonary arterial hypertension, and chronic thromboembolic arterial hypertension (CTEPH). In result, it was confirmed that rapid iloprost inhalation achieved the desired pulmonary vascular effects which were very comparable to those found in Example 3. Moreover, no adverse effects were observed other than the SAP and SVR changes which were mild and comparable to those observed after conventional iloprost treatment, i.e. slow inhalation of iloprost.

Example 5

Prophetic Example

In analogy to Example 3, further patients suffering from pulmonary arterial hypertension receive the same treatment with aerosolised iloprost, except that an inhalation device is used which is configured to deliver the aerosol, per breathing manoeuvre, during a nebulisation phase of 2 seconds followed by a period of one second in which aerosol-free air is emitted, so that the duration of the inhalation phase is 3 seconds. The exhalation phase is preset to be 3 seconds, and thus the total length of an average breathing manoeuvre is 6 seconds. Some patients receive single doses of 2.5 μg of iloprost using an iloprost solution having the strength of 10 μg/mL, others receive single doses of 5 μg of iloprost using an iloprost solution having the strength of 20 µg/mL; in both cases, the amount of liquid to be aerosolised and delivered is 0.25 mL.

The inhalation devices, which are of the type described as the third inhalation device (C) in Example 2 above, exhibit an output rate of about 0.5 mL/min, or about 8.33 µL/sec, respectively. In average, about 15 breathing manoeuvres are required to inhale a single dose of iloprost under these conditions. The total inhalation time in which the single dose is administered is about 90 seconds.

In result, it is expected that it is again confirmed that rapid iloprost inhalation achieves the desired pulmonary vascular effects which are comparable to those found in Example 3. Moreover, no adverse effects are observed other than mild SAP and SVR changes which are similar to those observed after conventional iloprost treatment, i.e. slow inhalation of iloprost. In conclusion, the efficient, safe, reliable and convenient administration of aerosolised iloprost by inhalation of a single dose within 2 minutes or less using more than 12 breathing manoeuvres is demonstrated.

The invention claimed is:

1. A method of treatment of pulmonary arterial hypertension which comprises administering to a patient in need thereof a composition comprising an active ingredient selected from iloprost and salts thereof, wherein an amount of the composition comprising an effective single dose from about 1.5 µg to about 5.0 µg of the active ingredient is provided using an inhaler adapted or configured to provide said dose in aerosolised form for inhalation within a period of less than 2 minutes, and wherein the aerosol is administered in more than 12 breathing manoeuvres.

2. The method of claim 1 wherein the aerosol is administered in 13 to 25 breathing manoeuvres.

3. The method of claim 1 wherein the average duration of a breathing manoeuvre is 6 seconds or less.

4. The method of claim 1 wherein the iloprost or salt thereof is administered using an inhaler which is adapted to emit the composition in aerosolised form at an output rate of 0.4 mL/min or more.

5. The method of claim 1 wherein the iloprost or salt thereof is administered using an inhaler which is adapted to emit the composition in aerosolised form at an output rate of 0.5 mL/min or more.

6. The method of claim 1 wherein the iloprost or salt thereof is administered using an inhaler Which is adapted to emit the composition in aerosolised form at a rate of 2.5 µg of iloprost per minute or more.

7. The method of claim 1 wherein the iloprost or salt thereof is administered using an inhaler which is adapted to emit the composition in aerosolised form at a rate of 5 µg per minute or more.

8. The method of claim 1 wherein the iloprost or salt thereof is administered using an inhaler which is adapted to emit, per inhalation phase, a predetermined volume of aerosol-free air immediately following a predetermined volume of the aerosol, wherein the predetermined volume of aerosol-free air is optionally emitted by the inhaler over a period of 0.2 to 2 seconds at the end of each inhalation phase.

9. The method of claim 1 wherein the iloprost or salt thereof is administered using an inhaler which is adapted to emit, per inhalation phase, a predetermined volume of aerosol-free air immediately following a predetermined volume of the aerosol, wherein the predetermined volume of aerosol-free air is emitted by the inhaler over a period of 1 to 3 seconds per inhalation phase.

10. The method of claim 4 wherein the inhaler is Selected from metered-dose inhalers, soft mist inhalers, and vibrating mesh nebulisers.

11. The method of claim 1 wherein the iloprost or salt thereof is administered at a strength of 10 µg/mL and the effective single dose is 2.5 µg, or wherein the strength is 20 µg/mL and the effective single dose is 5 µg.

12. A pharmaceutical kit comprising:
    (a) a composition comprising an active ingredient selected from iloprost or a salt thereof; and
    (b) an inhaler adapted for providing an amount of the composition comprising an effective single dose from about 1.5 µg to about 5.0 µg, of the active ingredient in aerosolised form for inhalation in more than 12 breathing manoeuvres and within a period of less than 2 minutes.

13. A pharmaceutical kit comprising:
    (a) a composition comprising an active ingredient selected from iloprost or a salt thereof; and
    (b) an electronic data storage means capable of controlling the operation of an inhaler so as to provide an amount of the composition comprising an effective single dose from about 1.5 µg to about 5.0 µg of the active ingredient in aerosolised form for inhalation in more than 12 breathing manoeuvres and within a period of less than 2 minutes.

* * * * *